US00PP37537P2

(12) United States Plant Patent
Knoblauch

(10) Patent No.: US PP37,537 P2
(45) Date of Patent: Jul. 21, 2026

(54) ***BEGONIA* PLANT NAMED 'BEYZ0014'**

(50) Latin Name: *Begonia hybrida*
Varietal Denomination: BEYZ0014

(71) Applicant: SYNGENTA CROP PROTECTION AG, Basel (CH)

(72) Inventor: Cathy Knoblauch, Whitecourt (CA)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/308,394

(22) Filed: Aug. 25, 2025

(51) Int. Cl.
*A01H 5/02* (2018.01)
*A01H 6/18* (2018.01)

(52) U.S. Cl.
USPC ..... Plt./343
CPC ..... *A01H 6/185* (2018.05)

(58) Field of Classification Search
USPC ..... Plt./343
CPC ..... A01H 5/02
See application file for complete search history.

*Primary Examiner* — Kent L Bell
(74) *Attorney, Agent, or Firm* — Dale Skalla

(57) ABSTRACT

A new *Begonia* plant named 'BEYZ0014' has a symmetrical upright, mounded habit, vivid orange double male flowers, and single vivid orange female flowers that bloom naturally from spring to fall. 'BEYZ0014' is characterized by its deep mahogany brown foliage with bright green veins.

1 Drawing Sheet

Botanical designation: *Begonia hybrida.*
Cultivar denomination: 'BEYZ0014'.

BACKGROUND OF THE NEW PLANT

The present invention comprises a new *Begonia* plant, botanically known as *Begonia hybrida*, and hereinafter referred to by the variety name 'BEYZ0014'.

'BEYZ0014' is a product of a planned breeding program in Whitecourt, Alberta, Canada. The new cultivar 'BEYZ0014' has a symmetrical compact habit, vivid orange double male flowers, and single vivid orange female flowers that bloom naturally from spring to fall. 'BEYZ0014' is characterized by its deep mahogany brown foliage with bright green veins.

'BEYZ0014' is the result of a planned pollination made in the fall of 2019 at the inventor's nursery in Whitecourt, Alberta, Canada. The female parent of the new cultivar is the unnamed seedling of proprietary origin, characterized by its light orange flowers. 'BEYZ0014' differs from the female parent by having darker orange flowers. The male parent of the new cultivar is a seedling of proprietary origin, having red flowers and a spreading habit.

The resulting seed was sown in fall 2019 in a controlled greenhouse environment in Whitecourt, Alberta, Canada and 'BEYZ0014' was selected as one flowering plant within the progeny of the stated cross in June of 2020.

The first act of asexual reproduction of 'BEYZ0014' was accomplished when vegetative stem cuttings were propagated from the initial selection in the inventor's nursery in July 2020.

BRIEF SUMMARY OF INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

A Plant Breeder's Right for this cultivar has not yet been applied for. 'BEYZ0014' has not been made publicly available prior to the effective filing date of this application, notwithstanding any disclosure that may have been made less than one year prior to the effective filing date of this application by the inventor or another who obtained 'BEYZ0014' directly from the inventor.

The following traits have been repeatedly observed and are determined to be basic characteristics of the new variety. The combination of these characteristics distinguishes this *Begonia* as a new and distinct variety.

1. 'BEYZ0014' has a upright, mounded and symmetrical habit.
2. 'BEYZ0014' achieves a height of about 26 cm.
3. 'BEYZ0014' achieves a width of about 30 cm.
4. 'BEYZ0014' blooms continuously from spring to fall.
5. 'BEYZ0014' has intensely colored vivid orange flowers.
6. 'BEYZ0014' has deep mahogany brown foliage with green veins and deep reddish undersides.

BRIEF DESCRIPTION OF THE PHOTOGRAPHS

Figure 1:
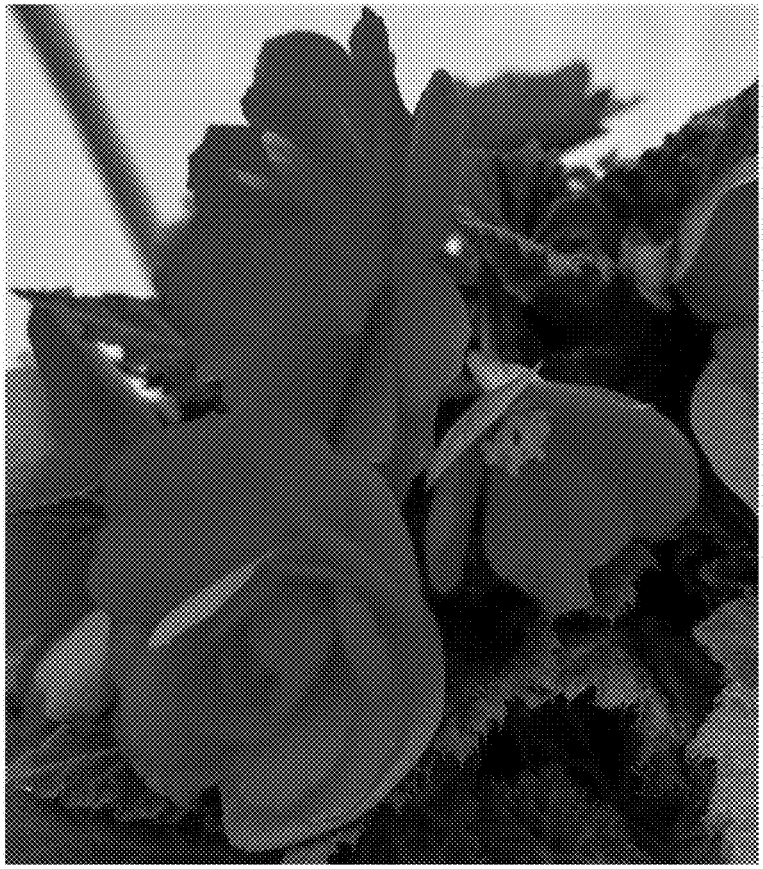
Figure 2:
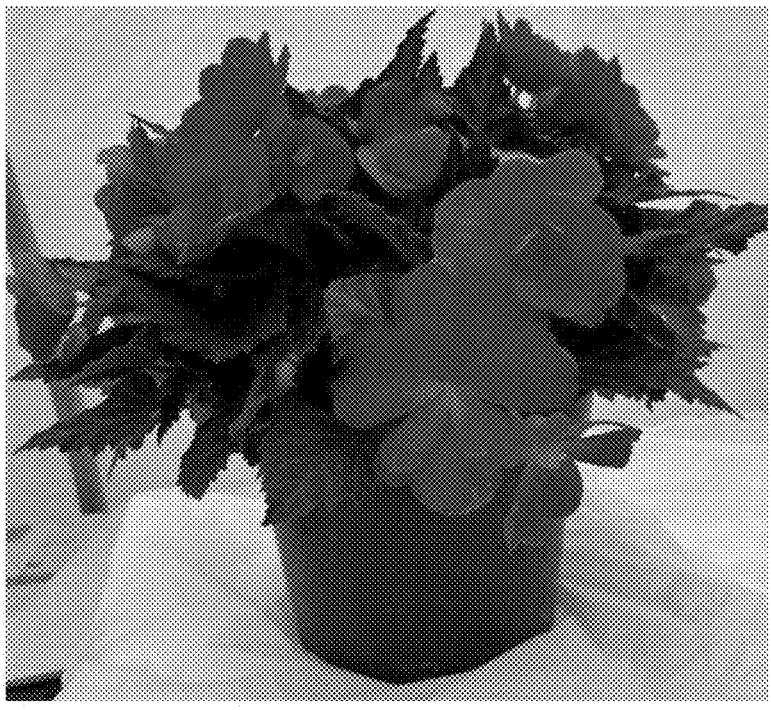

The accompanying photographic drawings show typical flower and foliage characteristics of 'BEYZ0014' with colors being as true as possible with an illustration of this type. The photographic drawings taken when the plant was 5 months old show in FIG. 1 a close view of an inflorescence taken in August 2025 in Whitecourt, Alberta, Canada, and in FIG. 2 a whole flowering plant taken in August 2025 in Whitecourt, Alberta, Canada.

DETAILED BOTANICAL DESCRIPTION

The plant descriptions and measurements were taken in Whitecourt, Alberta, Canada in August 2025. The plants were approximately 5 months old and were growing in 8-inch pots, one plant per pot, in a greenhouse.

Color references are made to The Royal Horticultural Society Colour Chart (R.H.S.) 2001.

TABLE 1

DIFFERENCES BETWEEN THE NEW VARIETY AND A MOST SIMILAR VARIETY

| | 'BEYZ0014' | Nonstop ® Mocca Orange, unpatented |
|---|---|---|
| Foliage and flowers: | Smaller leaves and flowers | Larger leaves and flowers |
| Habit: | Smaller, symmetrical | Larger, asymmetrical |
| Branching: | Vigorous basal and lateral branching | Slower, asymmetrical and irregular branching |

Propagation:

*Type*.—Vegetative tip cuttings.

*Time to initiate roots, summer and winter*.—About 15 days.

*Time to produce a rooted young plant summer*.—About 30 to 40 days.

*Time to produce a rooted young plant, winter*.—About 40-50 days.

*Root description*.—Fibrous, moderately branched.

*Rooting habit*.—Moderately vigorous.

Plant description:

*Plant and growth habit*.—Upright, mounded and freely branched.

*Plant height, soil level to top of foliar plane*.—About 24 cm.

*Plant height, soil level to top of floral plane*.—About 26 cm.

*Plant width*.—About 30 cm.

*Lateral branch description*.—Upright, freely branching.

*Length*.—About 10 cm.

*Diameter*.—About 8 mm.

*Internode length*.—About 2 cm.

*Strength*.—Strong.

*Aspect*.—Upright, symmetrical.

*Texture and luster*.—Pilose, matte.

*Color, developing*.—Nearest RHS 148C.

*Color, developed*.—Nearest RHS 195A.

Leaf description:

*Arrangement*.—Alternate.

*Length*.—About 10 cm.

*Width*.—About 5 cm.

*Shape*.—Lanceolate.

*Apex*.—Sharply acute.

*Base*.—Obtuse.

*Margin*.—Double serrate.

*Texture and luster, upper surface*.—Pilose, semi glossy.

*Lower surface*.—Smooth, glabrous.

*Venation pattern*.—Palmate, pinnate.

*Upper leaves, developed*.—141A.

*Upper leaves, developing*.—143A.

*Lower leaves, developed*.—182B.

*Lower leaves, developing*.—159A.

*Venation color, upper surface*.—Nearest RHS 143C.

*Venation color, lower surface*.—Nearest 142C.

Petioles:

*Length*.—About 4 cm.

*Diameter*.—About 5 mm.

*Texture and luster, upper and lower surfaces*.—Pilose, semi-glossy.

*Strength*.—Strong.

*Color, upper surface*.—Nearest RHS 30C.

*Color, lower surface*.—Nearest RHS 2D.

Stipules:

*Quantity per leaf*.—Two.

*Length*.—About 1 cm.

*Width*.—About 4 mm.

*Shape*.—Triangular.

*Apex*.—Sharply acute.

*Base*.—Obtuse.

*Margins*.—Denticulate.

*Color, upper and lower surfaces*.—Nearest RHS 1D.

Flower description:

*Flowering habit*.—Continuous.

*Fragrance*.—None.

*Natural flowering season*.—Spring to fall.

*Flower longevity*.—About 30 days.

*Inflorescence height* (*including peduncle*).—About 10 cm.

*Flower buds, female flowers*.—

*Length*.—About 2 cm.

*Diameter, flattened*.—About 1.5 cm.

*Shape*.—Ovate.

*Texture and luster*.—Smooth, matte.

*Color, upper surface*.—Nearest RHS 30B.

*Color, lower surface*.—Nearest RHS 28A.

*Flower buds, male flowers*.—

*Length*.—About 4 cm.

*Diameter, flattened*.—About 2.5 cm.

*Shape*.—Broadly ovate.

*Texture and luster*.—Smooth, matte.

*Color, upper surface*.—Nearest RHS 30A through RHS 34A.

*Color, lower surface*.—Nearest RHS 31B through RHS 32C.

*Female flowers length*.—About 8 cm.

*Depth*.—About 9 cm.

Tepals female flowers:

*Quantity per flower and arrangement*.—5 arranged in a single whorl.

*Length, tepals*.—About 4 cm No inner tepals, one single whorl in female flowers.

*Width, female tepals*.—About 2 cm.

*Shape, female tepals*.—Obovate.

*Apex, female tepals*.—Roundly obtuse.

*Base, female tepals*.—Acute.

*Margin, female tepals*.—Entire.

*Texture and luster, female tepals, upper surface*.—Smooth, matte.

*Texture and luster, female tepals, lower surface*.—Smooth, matte.

*Color, Female flowers, tepals*.—

*When opening, upper surface*.—Nearest RHS 30A through RHS 34A.

*When opening, lower surface*.—Nearest RHS 31B through RHS 32C.

*Fully opened, upper surface*.—Nearest RHS 31B through RHS 32C.

*Fully opened, lower surface*.—Nearest RHS 31B through RHS 32C.

*Tepaloids*.—None observed on female flowers.

*Male flowers.*—
*Size.*—Width About 8 cm.
*Depth.*—Length About 8 cm.

Tepals:
*Quantity per flower and arrangement.*—About 40 arranged on about 8 whorls.
*Length, inner tepals.*—About 2 cm.
*Length, outer tepals.*—About 4 cm.
*Width, inner tepals.*—About 1.5 cm.
*Width, outer tepals.*—About 4 cm.
*Shape, inner tepals.*—Obovate.
*Shape, outer tepals.*—Broadly ovate.
*Apex, inner and outer tepals.*—Obtuse, ovate.
*Base, inner and outer tepals.*—Ovate, obovate.
*Margin, inner and outer tepals.*—Entire.
*Texture and luster, inner and outer tepals, upper surface.*—Smooth, matte.
*Texture and luster, inner and outer tepals, lower surface.*—Smooth, matte.
*Color, inner tepals.*—
*When opening, upper surface.*—Nearest RHS 30A through RHS 34A.
*When opening, lower surface.*—Nearest RHS 31B through RHS 32C.
*Fully opened, upper and lower surfaces.*—Nearest RHS 31B through RHS 32C.
*Color, outer tepals.*—
*When opening, upper surface.*—Nearest RHS 30A through RHS 34A.
*When opening, lower surface.*—Nearest RHS 31B through RHS 32C.
*Fully opened, upper surface.*—Nearest RHS 30A through RHS 34A.
*Fully opened, lower surface.*—Nearest RHS 31B through RHS 32C.
*Tepaloids.*—None observed on male flowers.

Peduncles:
*Length.*—About 5 cm.
*Diameter.*—About 4 cm.
*Angle.*—Acute.
*Strength.*—Strong.
*Texture and luster.*—Pilose, semi glossy.
*Color, upper and lower surfaces.*—Nearest RHS 1D through RHS 28A.

Pedicels, female flowers:
*Length.*—About 2.5 cm.
*Diameter.*—About 2 mm.
*Angle.*—Acute.
*Strength.*—Moderate.
*Texture and luster.*—Pilose, semi-glossy.
*Color, upper surface.*—Nearest RHS 22D through RHS 29B.
*Color, lower surface.*—Nearest RHS 23D.

Pedicels, male flowers:
*Length.*—About 1.5 cm.
*Diameter.*—About 3 mm.
*Angle.*—Acute.
*Strength.*—Moderately strong.
*Texture and luster.*—Smooth, glossy.
*Color, upper surface.*—Nearest RHS 32D.
*Color, lower surface.*—Nearest RHS 165D.

Flower bracts:
*Quantity per flower and arrangement.*—2, opposite.
*Length.*—About 1.5 cm.
*Width.*—About 1.5 cm.
*Shape.*—Broadly ovate.
*Apex.*—Roundly obtuse.
*Base.*—Cordate.
*Margin.*—Denticulate.
*Texture and luster, upper and lower surfaces.*—Pilose, glossy.
*Color, upper surface.*—RHS 144D through RHS 172C.
*Color, lower surface.*—RHS 144C through RHS 169A.

Reproductive organs:
*Androecium.*—
*Stamen quantity per flower.*—None observed.
*Filament length.*—None observed.
*Filament color.*—None observed.
*Anther size.*—None observed.
*Anther shape.*—None observed.
*Anther color.*—None observed.
*Amount of pollen.*—None observed.
*Pollen color.*—None observed.
*Gynoecium.*—
*Quantity per flower.*—One.
*Pistil length.*—About 2 mm.
*Stigma diameter.*—About 1 cm.
*Stigma shape.*—Bifurcated spiral.
*Stigma color.*—Nearest RHS 23B.
*Style length.*—About 2 mm.
*Style color.*—Nearest RHS 21C.
*Ovary color.*—Nearest RHS 154D.
*Seeds and fruits.*—None observed.

Pathogen & pest resistance: To date, resistance to pathogens and pests common to *Begonia* plants has not been observed on plants of the new *Begonia.*

Temperature tolerance: Plants of the new *Begonia* have been observed to tolerate high temperatures of about 30° C. and to be suitable for USDA Hardiness Zones 7 to 9.

What is claimed is:

1. A new and distinct variety of *Begonia* plant named 'BEYZ0014' substantially as illustrated and described herein.

* * * * *